United States Patent
Marinkovich

(12) 
(10) Patent No.: US 7,112,328 B2
(45) Date of Patent: Sep. 26, 2006

(54) COMPOSITION FOR TARGETED CELL TREATMENT

(76) Inventor: Vincent Marinkovich, 26 Botany Ct., Redwood City, CA (US) 94062

( * ) Notice: Subject to any disclaimer, the term of this patent is extended or adjusted under 35 U.S.C. 154(b) by 1050 days.

(21) Appl. No.: 09/764,224

(22) Filed: Jan. 16, 2001

(65) Prior Publication Data

US 2003/0108555 A1 Jun. 12, 2003

Related U.S. Application Data

(63) Continuation-in-part of application No. PCT/US99/15716, filed on Jul. 12, 1999.
(60) Provisional application No. 60/093,084, filed on Jul. 16, 1998.

(51) Int. Cl.
*A61K 39/395* (2006.01)
*A61M 36/14* (2006.01)

(52) U.S. Cl. .................. 424/178.1; 424/1.11; 424/198.1

(58) Field of Classification Search .............. 424/178.1, 424/1.11, 198.1
See application file for complete search history.

(56) References Cited

PUBLICATIONS

Gura (Science, v278, 1997, pp. 1041–1042).*
Weiner L.M., Seminars Oncology, vol. 26, No. 4, Suppl 12, pp. 41–50, 1999.*
Kranz et al (PNAS USA Sep. 1995; 92:9057–9061).*

\* cited by examiner

*Primary Examiner*—G. Nickol
*Assistant Examiner*—C. Yaen
(74) *Attorney, Agent, or Firm*—DLA Piper Rudnick Gray Cary US LLP

(57) ABSTRACT

Compositions, vaccines and kits for cancer immunotherapy are described. The compositions, vaccines and kits may include transfer factor. The compositions, vaccines and kits also include modified monoclonal antibodies directed to cancer cells, other specific cancer receptor agonists, or viruses which infect cancer cells. The invention is also directed to methods of cancer immunotherapy using the compositions and vaccines of the invention.

9 Claims, No Drawings

COMPOSITION FOR TARGETED CELL TREATMENT

CROSS-REFERENCE TO RELATED APPLICATIONS

This is an application claiming priority as a continuation-in-part to International application No. PCT/US99/15716, filed Jul. 12, 1999 designating the United States and claiming priority to U.S. Provisional Application No. 60/093,084, filed Jul. 16, 1998.

FIELD OF THE INVENTION

This invention relates to the field of therapeutic agents in medicine. In particular, this invention relates to the field of cancer immunotherapy.

BACKGROUND OF THE INVENTION

It is generally believed that the emergence of cancer in an individual is the result of a confluence of factors: an inherited genetic weakness, an environmental insult such as radiation or a chemical injury, and the failure of that individual's immune system to respond to the emerging cancer. While significant progress has been made in cancer research, many forms of cancer still remain incurable. For example, pancreatic cancers are among the most lethal of all cancers, because they grow rapidly, metastasize most often before the cancer is discovered, and are resistant to all known modes of therapy.

Monoclonal antibodies have been recognized as potentially important agents to use in diagnosing and treating cancer. Monoclonal antibodies react with a single foreign substance (antigen) as do all antibodies, but their most valued characteristics are that they can be selected and created to react with a simple desired antigenic epitope, they can be made in large quantities, and they are relatively innocuous when injected into the human host. The techniques for creating monoclonal antibodies were elaborated thirty years ago, although refinements in technology continue to date.

Early cancer researchers prepared modified monoclonal antibodies which recognized and reacted with cancer cells for cancer treatment. These monoclonal antibodies included a radioactive isotope or a poison designed to inhibit the growth of the cancer. The modified monoclonal antibodies were injected into a patient with cancer where they would traverse the body and react with the cancer cells regardless of their location. The monoclonal antibodies were designed as the specific delivery vehicle with which to take a killing function to the cancer.

FR2 128 267 A (T. Asada) dated Oct. 20, 1972, describes the use of mumps virus for the treatment of cancer.

R. Crusinberry, et al. Seminar in Surgical Oncology, Vol. 7, no. 4, Jul. 1991, pages 221–229, New York, N.Y., USA describes the use of a transfer factor, alone, or in combination with BCGor chemotherapy in cancer immunotherapy.

U. Prasad, et al. Biotherapy, vol 9, no. 1–3, 1996, pages 109–115 describes the use of transfer factors as an adjuvant therapy in combination with chemotherapy or radiotherapy.

L. Basutti, et al. Journal of Experimental Pathology, vol. 3, no. 4, 1987, pages 565–568 describes the use of transfer factors as an adjuvant therapy in combination with chemotherapy or radiotherapy.

EPO 010 738A (A/S Alfred Benzon) 14 May 1980 (1980 May 14) describes the use of transfer factor therapeutically by parental administration in human beings to obtain immunity directed against an antigen which is pathogenic in man, such as cancer cells or extracts thereof.

The initial enthusiasm for the use of monoclonal antibodies in treating cancer cooled when it became clear that an effective killer function was not easy to develop and that monoclonal antibodies needed further modifications to be effective at treating cancer.

There is thus a strong need to develop new cancer therapies. In particular, there is a need to improve monoclonal antibody cancer therapies as well as provide specific cancer receptor agonists other than monoclonal antibodies in cancer therapies.

SUMMARY OF THE INVENTION

In order to meet these needs, the present invention is directed to compositions and methods for cancer immunotherapy.

This invention is directed to compositions for cancer immunotherapy. The compositions may include a virus that infects cancer cells, monoclonal antibodies that recognize cancer cells, or other specific cancer cell receptor agonists to which a specific T-cell activity can be generated. The administration of the composition is accompanied by the administration of transfer factor as a means of conferring upon the patient a specific T-cell response against a composition antigen. The transfer factor may be administered before, during or after the administration of the cancer immunotherapy composition.

This invention is also directed to vaccines for cancer immunotherapy. The vaccines may comprise a monoclonal antibody and transfer factor or a virus and transfer factor or a specific cancer cell receptor antagonist and transfer factor. The patient may be previously immunized to the specific antigenic component of the composition molecule by standard immunogenic techniques. The antigen may also be selected to correspond to a T-cell activity the patient already possesses. The components of the vaccine may be administered at different times in sequence.

The monoclonal antibodies of the invention may be conjugated to an antigen. The antigen will be an antigen that predominately elicits a cell mediated immune response rather than a hummoral immune response. The antigen may be a virus to which the patient may be immunized or to which the patient has already developed an immune response. Such viruses include the mumps virus, the hepatitis virus and the encephalitis virus among others. The antigen may be Aspf1 from the fungus aspergillus, tuberculo protein, coccidioidin, or other antigens known to elicit a major T-cell (delayed immunity) response in humans.

The vaccines may also comprise a virus. The virus will be a virus to which the patient has already developed an immune response. Such viruses include the mumps virus, the hepatitis virus and the encephalitis virus.

The viruses of the invention may also be modified to include an antigen such as Aspf1 from the fungus aspergillus, tuberculo protein, coccidioidin, or other antigens known to elicit a major T-cell (delayed immunity) response in humans.

The invention is also directed to kits whose components are useful in cancer immunotherapy. The kits may include transfer factor, viruses and/or monoclonal antibodies. The kit may also include components useful in administering the kit components.

The invention is also directed to methods of administrating the compositions and vaccines of the invention. In the methods of the invention, the transfer factor may be administered simultaneously or at different times from the other components of the vaccine.

DETAILED DESCRIPTION OF THE INVENTION

Definitions

To ensure a complete understanding of the invention the following definitions are provided:

Antibody: A protein which is produced as a result of the introduction of an antigen and which has the ability to combine with the antigen that stimulated its production.

Monoclonal Antibody: Monoclonal antibodies are chemically and immunologically homogenous antibodies produced by hybridomas. Monoclonal antibodies useful in the invention include monoclonal antibodies directed to various epitopes on cancer cells. Such cancer cells include lung, pancreas, liver, cervical, kidney, brain, breast and spleen cancer cells. These antibodies can be humanized. Such antibodies are commercially available and include of 17-1A (Panorex), CC49, anti EGFr surface factor mab for prostate cancer; anti MC-10 antigen mab for breast cancer; available from the National Cancer Institute or from commercial producers, anti HER2 (Herceptin, Genentech) for breast cancer; anti CD20 antigen mab (Rituxan, Genentech) for non-Hodgkin's lymphoma; NR-LU-10 mab for advanced cancers and MDX-H210 mab for metastic adenocarcinoma. Monoclonal antibodies directed to cancer cell antigens are also available from Biodesign International, 105 York Street, Kennebunk, Me. 04043, USA and include: Cancer Antigen CA-50; Cancer Antigen CA125 (Ovarian Cancer); Cancer Antigen CA15-3 (Breast Cancer); Cancer Antigen CA19-9 (Gastrointestinal Cancer); Cancer Antigen CA242 (Gastrointestinal Cancer); Carcinoembryonic Antigen (CEA); Carcinoma Associated Antigen; Melanoma Antigen; Melanoma Associated Antigen 100-7 kDa; Melanoma Associated Antigen 25-110 kDa; and Melanoma Associated Antigen 450+/250 kDa.

Other monoclonal antibodies directed to cancer cell antigens are available from Yes Biotech Laboratories Ltd., 7035 Fir Tree Drive, Unit 23, Mississauga, Ontario, Canada and include: Anti-Human Lung Carcinoma: CHALU12, CHALU12 and CHLG-26; Anti-Human Hepatocellular Carcinoma: CHALV1, CHALV2 and CHALV3; Anti-Human Alpha Fetoprotein: B6, G7; Anti-Human Colorectal Carcinoma: Y94; Anti-Human Gastric Carcinoma: BY-1 (3H11); Anti-Human Colorectal Carcinoma/CD3 (Bispecific): BS-1; Anti-Human PSA: CHYH1, CHYH2; Anti-Human PMA: YPMA-1, YPMA-2; Anti-Human PSP: YPSP-1, YPSP-2; and Anti-Human PSMA: Y-PSMA1, YPSMA2.

Antigens: Antigens are molecules which initiate an immune response. Antigens useful in the invention are those which initiate a cell-mediated immune response as compared to a humoral immune response. Antigens may include Asp f1 or other fungal antigens, viruses or virus components, tuberculo protein, coccidioidin, BCG, etc.

Viruses: Viruses are genetic elements enclosed by a protein coat that are capable of infecting cells and moving from one cell to another to cause disease. Viruses useful in the invention are those which infect cells which have become cancerous and with which the patient may or may not have already developed an immune response. Viruses useful in the invention include the mumps virus which targets cells of the testes, pancreas, salivary glands and parotid glands; the hepatitis virus which targets liver cells; the encephalitis virus which targets brain cells; the Rubella virus; the Measles virus and the Varicella virus.

Transfer factor: Transfer factor is a dialyzable extract of immune lymphocytes that is capable of transferring cell-mediated immunity in humans and in other animal species. Immunized transfer factor is transfer factor that has been isolated from a host that has been immunized with an antigen. Normal transfer factor is transfer factor that has been isolated from hosts who have not been specifically immunized but who have generated the necessary cellular immunity through natural exposure.

Vaccine: A vaccine is a preparation used as a preventive inoculation to confer immunity against a disease such as cancer. A vaccine may include multiple components administered at different time periods. The components of the vaccine may be in the pure state or in combination with other materials. In addition, the vaccine components may be in combination with salts and buffers, may be in a dried state, in a solvent as a precipitate or in a aqueous solution.

Taking into account these definitions, the present invention relates to the use of immunotherapy in the treatment of cancer. In particular, the present invention is directed to the use of modified monoclonal antibodies in the treatment of cancer. This invention is further directed to the use of viruses in the treatment of cancer. The invention is further directed to the selection of antigens for coupling to antibodies and viruses to which the patient has already initiated a cellular immune response or to which a cellular immune response can be induced.

Cancer Immunotherapy

The aim of cancer immunotherapy is to bolster a patient's immune system so that it is better able to combat cancer and remove cancer cells.

Immune responses involve a complex series of events. Antigens of an invading microorganism must come into contact with cells of the immune system (macrophages and lymphocytes) to initiate an immune response specific for the foreign material. The cells that respond are precommitted, because of their surface receptors, to respond to a particular epitope on the antigen in a process known as acquired immunity. This acquired immunity response takes two forms that usually develop in parallel. The part played by each form will depend on a number of factors including the nature of the antigen, the route of entry and the individual who is infected. The existence of the two forms of acquired immunity—humoral and cell-mediated—results from the presence of the two major classes of lymphocyte: B-cells and T-cells.

Humoral Immunity

Humoral immunity depends on the appearance in the blood of glycoproteins known as antibodies or immunoglobulins. These molecules are produced by plasma cells, that have developed from B-cells, and combine specifically with the antigen that stimulated their production. This union can lead to a number of consequences. For example, the antigen molecules or particles may become clumped, their toxic potential may be neutralized and their uptake by phagocytes and subsequent digestion facilitated whilst antigens such as cells or bacteria may also be lysed as a result of complement activation.

In the present invention, it is important to reduce or minimize the humoral immunity response in order to provide time for the modified monoclonal antibodies and viruses of the invention to seek out their target cancer cells before they are inactivated by the immunoglobulins produced by the humoral immune response.

Cell-Mediated Immunity

The term cell-mediated immunity was originally coined to describe localized reactions to organisms mediated by T-lymphocytes and phagocytes rather than by antibody. It is now used to describe any response in which antibody plays a subordinate role. Cell-mediated immunity depends mainly on the development of T-cells that are specifically responsive to the inducing agent and is generally active against intracellular organisms. The effector cells can interact directly with the infected cell and destroy it, i.e., a cytotoxic effect, or produce molecules that stimulate other cells to destroy the intracellular parasite.

In the present invention, it is important to increase and maximize the cell-mediated immune response in order to maximize the chances of destroying the cancer cells.

Cell mediated immune responses are not brought about by circulating antibody but by sensitized lymphoid cells. A normal cell-mediated immune response develops when first exposure to the antigen gives rise to a population of antigen-specific memory T-lymphocytes. These cells continuously circulate around the body until they come across the antigen expressed on the surface of an antigen-presenting cell in association with MHC class II. The cells are stimulated by this interaction to proliferate and release lymphokines. The lymphokines are responsible for the cell-mediated host defense mechanisms that involve not only the attraction and activation of macrophages but also the stimulation of precursor cytotoxic T-cells into effector cells. These events lead to the elimination of the foreign material, in this invention the specific cancer receptor cell agonist, (e.g., monoclonal antibody) and/or virus associated with the cancer cell.

This invention is directed to the use of modified monoclonal antibodies, viruses and modified viruses to target cancer cells and trigger a cell-mediated immune response in order to destroy the cancer cells.

Monoclonal Antibodies and Cancer Immunotherapy

In one embodiment of the invention, monoclonal antibodies to cancer cells are prepared and modified. The monoclonal antibodies of the invention are generally commercially available. Such monoclonal antibodies are preferably humanized monoclonal antibodies. Humanized monoclonal antibodies are known to produce reduced humoral immune responses as compared to the responses of mouse monoclonal antibodies. This difference is thought to result from the humanized antibodies being less dissimilar or foreign to the body's immune system so as to induce a reduced immune response. The monoclonal antibodies of the invention recognize epitopes specific for cancer cells. The monoclonal antibodies are modified by procedures well known in the art to conjugate one or more antigens to the monoclonal antibody. The antigens are selected based upon their ability to maximize the cell-mediated immune response while minimizing the humoral immune response.

In this invention, an antigen to which a patient's immune system may already have a potent T-lymphocyte reactivity is attached to a monoclonal antibody which recognizes a specific cancer cell epitope. This epitope will initiate a vigorous T-cell attack on the monoclonal antibody. The monoclonal antibody will be selected for its ability to seek out a cancer (e.g., monoclonal antibody 17-1A or CC49 for pancreatic carcinoma). Through administration in the form of a vaccine, the modified monclonal antibody delivers an antigen to the cancer in vivo. Once the modified monoclonal antibody attaches to the cancer cell, it makes the cancer cell represent a recognized foreign material to the T-cell population. The destructive power of the T-cell is formidable and can easily destroy a cancer cell if activated in that direction.

Asp f1 as an Antigen

One example of an antigen useful in the invention which can be attached to the monoclonal antibody is the antigen Asp f1. This antigen is derived from the fungus aspergillus fumigatus which is a potent human pathogen whose threat is well controlled by a normal immune system because of pre-existing immunity, both cellular and humoral. However, this antigen is deadly for patients who are immunologically compromised. In this invention, live aspergillus organisms are not injected into the patient. Instead, the extracted protein or glycoprotein antigens from the organisms coupled to monoclonal antibodies which recognize cancer cell epitopes and are injected into the patient.

The antigen Asp f1 is the most potent of the antigens present on the fungus aspergillus. All normal individuals have developed a strong T-cell response to this antigen by the time they reach adulthood. It is available as a purified fraction of the fungal lysate and as a product of recombinant technology (i.e., manufactured in bioengineered yeast organisms). The antigen can easily be attached to monoclonal antibodies by procedures well known in the art.

Recombinant aspergillus antigens are commercially available in pure form and are preferable to crude extracts of the fungus. However, in an alternative embodiment, the latter can be conjugated to the monoclonal antibody. In yet another embodiment, purified or crude extracts of other fungi or bacteria are conjugated onto the monoclonal antibodies to deliver a recognizable antigen to the cancer surface to which a strong killer T-cell response would be directed.

The process of attaching an antigen to an antibody without altering the receptor (cancer cell) binding characteristics of the antibody is well known to immunochemists. Such procedures involve the purification of the antibody, dialysis and/or column chromatography and equalization of the purified antibody in buffer. Next, the antigen is conjugated to the antibody. Finally, the conjugated antibody is purified from unconjugated antigen. The procedure is outlined in detail below.

Once the Asp f1 or other antigens are conjugated to the monoclonal antibodies, the product is injected intravenously. The modified monoclonal antibody may be supplemented by the addition of immunized and/or normal transfer factor as discussed below. The antibody and the transfer factor are administered in the form of a vaccine where the antibody and transfer factor may be administered at different times. The transfer factor induces or increases the immune response.

Viruses as Antigens

In another embodiment, the antigen attached to the monoclonal antibody may be a virus. The virus is selected based upon the patient having a well developed immune response to the virus. In yet another alternative embodiment, the virus may be administered directly because it is known to selectively attach to the cells which are malignant. The virus may also be modified to include additional antigens. Preferably, the virus is a mumps virus for pancreatic, salivary or testicular cancers.

The process of attaching a virus to a monoclonal antibody without altering the receptor (cancer cell) recognition characteristics of the antibody is well known to immunochemists as outlined in detail below.

Viruses and Cancer Immunotherapy

Viruses may be injected directly as a form of cancer immunotherapy. Viruses useful in the invention are those which infect cells susceptible to cancer and with which the patient has developed an immune response, for example, the mumps virus. The mumps virus is known to be reactive with certain secretory cells, including those of the pancreas, the salivary glands of the mouth, and the testes. The normal adult has a well developed immunity to the mumps virus throughout life. The procedure of this invention is utilized as a means to redirect a cancer patient's immune system to the presence of mutated cancer cells in the body so that individual's T cells can destroy the cancerous mutation and restore health.

In an alternative embodiment of the invention, the mumps virus is injected in heavy doses and repeatedly so that the mumps virus can become attached to the cancer cells of the cancer patient. In the case of pancreatic cancer patients, the virus becomes attached to the pancreatic cancer cells. The mumps virus may be administered in the form of a vaccine and may be supplemented by the addition of immunized and/or normal transfer factor. The attachment of the mumps virus to the pancreatic cancer cells causes these cancerous cells to be identified as mumps viruses to the immune system. The addition of transfer factor further increases this response. Consequently, a vigorous immune response is unleashed against the virus (cancer). In this embodiment, the immune response is so massive that it destroys the primary cancer in the pancreas and also searches for, finds and destroys the metastatic cells as well.

In another alternative embodiment, the virus may be the hepatitis virus for the treatment of liver cancer since the hepatitis virus targets liver cells. In yet another alternative embodiment, the virus may be the encephalitis virus for the treatment of brain cancer since the encephalitis virus targets brain cells.

The viruses of the invention may be coupled to antigens by procedures well known in the art. In this embodiment, the antigens will be selected based upon their ability to elicit a cellular immune response as described above for monoclonal antibodies. A preferred antigen is asp f1.

The process of attaching an antigen to a virus without altering the receptor (cancer cell) recognition characteristics of the virus is well known to chemists as outlined in detail below.

Conjugation Procedure

Conjugation procedures are well known in the art of chemistry, biochemistry and immunochemistry. The general procedures are applicable to the conjugation of antigens, including viruses, to monoclonal antibodies and the conjugation of antigens to viruses.

Because most monoclonal antibodies, viruses and antigens contain both exposed lysines and carboxyl groups, EDC (1-Ethyl-3-[3-Dimethylamino propyl] Carbodiimide Hydrochloride) conjugation is a perferred method of conjugation. The carbodiimide moiety of EDC initially reacts with available carboxy groups on either the monoclonal antibody, virus and/or the antigen to form an active O-acylurea intermediate. This unstable intermediate reacts with a primary amine to form an amide bond with the release of a soluble urea derivative. The reaction usually takes less than 2 hours.

In general, EDC coupling is a very efficient, one-step method for forming a wide variety of antigen-monoclonal antibody, virus-monoclonal antibody and virus-antigen conjugates. Conjugation may occur at either the C- or N-terminal of the peptides or at any carboxyl- or amine-containing side chains.

Conjugation between monoclonal antibodies and antigens can readily be achieved with EDC by the following procedure. This procedure is also readily applicable to virus-antigen conjugation and virus-monoclonal antibody conjugation and may include the following steps.

1. Reconstitute 2 mg of monoclonal antibody with 200 μl deionized water.
2. Dissolve up to 2 mg of the antigen to be coupled in 0.5 ml of conjugation buffer (0.1 M MES, 0.9 M NaCl, 0.02% $NaN_3$, pH 4.7).
3. Add the 500 μl of antigen solution to the 200 μl antibody solution.
4. Dissolve 10 mg EDC in 1 ml deionized water and immediately add 50 μl of this solution to the antigen-monoclonal antibody solution.
5. Incubate the solution for 2 hours at room temperature. Remove any precipitate by centrifugation before further purification.
6. Purify the conjugate by gel filtration. Dialysis can also be used as an alternative to gel filtration desalting to prevent loss of sample and clogging of the desalting column when coupling very hydrophobic peptides to the carrier.
7. If the conjugate is to be stored for more than a few days, sterile filter the conjugate fractions and store them in a sterile container at 4° C. or keep them frozen at −20° C.

Other cross-linking agents are useful in antigen-monoclonal antibody, virus-monoclonal antibody and virus-antigen conjugation, for example, N-hydroxysuccinimide and N-hydroxysulfosuccinimide. The heterobifunctional crosslinker SMCC and sulfo-SMCC available from Pierce Chemical Company also have general utility in preparing conjugates. Maleimide-antigen derivatives can also be prepared. Furthermore, glutaraldehyde and metaperiodate derivatives can be prepared.

Maleimide activated antigen is prepared using the heterobifunctional crosslinker sulfo-SMCC available from Pierce Chemical Company. This reagent contains N-hydroxysulfosuccinimide (sulfo-NHS) and maleimide functional groups. The sulfo-NHS ester is reacted with a primary amine on the antigen to form a stable amide bond. After this first conjugation step, the antigen will have maleimide groups on its surface that are reactive toward sulfhydryl groups to form stable thioether bonds on the monoclonal antibody or virus. Once reacted, the antigen-monoclonal antibody conjugate or virus-antigen conjugate can be purified as discussed above.

Hetero-cross-linked antibodies may also be prepared using the heterobifunctional agent succinimidyl-3-(2-pyridyldithiol) propionate as described by Titus, et al., J. Immunol. 138:4018.

Transfer Factor

The monoclonal antibodies and viruses of this invention can be administered along with transfer factor. Transfer factor is utilized to increase the immune response. Transfer factor may be administered along with the virus or monoclonal antibody, before the addition of the virus or monoclonal antibody or after addition of the virus or monoclonal antibody.

Transfer factor is an extract from the peripheral blood lymphocytes of normal and immunized individuals which when injected into another individual confers upon the recipient the immunity of the donor's lymphocytes in the form of activated T-lymphocytes. Transfer factor may be isolated and purified by procedures well known in the art. Such procedures include those described in U.S. Pat. Nos. 4,816,563 and 5,840,700.

Transfer factor can be administered either by injection or can be administered orally. Oral administration is via pill or capsule. Injection of transfer factor can be intravenously, intramuscularly or subcutaneously or a combination of routes.

When injected, the dose of transfer factor required to impart immunity or increase the immune response in a human is between approximately 1 ng and 500 ng with a preferred does range of between 25 ng and 250 ng with a most preferred dose of approximately 50 ng.

Monoclonal Antibodies and Transfer Factor

If the patient lacks the required immune activity against the antigenic epitope on the monoclonal antibody, the patient's immune system is passively sensitized to that epitope with transfer factor from a sensitized individual. The use of transfer factor from immunized donors to confer such T-cell activity on the recipient is an additional maneuver to enhance the likelihood of a successful destruction of all cancer cells by the patient's own T-cell attack.

As discussed above, transfer factor is an extract of peripheral blood lymphocytes which can confer on the recipient the cellular immune activity (T-cell) of the donor. Thus, in an alternative embodiment of the invention, a patient without significant T-cell activity against an antigen (e.g., Asp f1) could be passively immunized for killer T-cell function with the transfer factor from an immunized donor or a normal donor selected for his existing strong T-cell activity against Asp f1.

Viruses and Transfer Factor

Most normal adults have in their lymphocytes and consequently in their transfer factor an immune memory of the antigens and/or viruses of this invention, including the mumps virus. By extracting transfer factor from normal donors and injecting transfer factor into the patient with cancer, including pancreatic cancer, it will give the patient a more vigorous anti-virus immunity. Transfer factor is extracted by procedures described in the Example section.

In this invention, patients with cancer, particularly pancreatic cancer are injected with mumps virus followed by transfer factor from normal and recently immunized donors to focus a killer T-cell immune activity against the mumps virus and, consequently, against the cancer. The treatment program is continued until the cancer is completely destroyed and the patient restored to health.

Kits

The vaccines of the invention may be supplied in the form of a kit. The kit would include as a first component a monoclonal antibody or a virus. The monoclonal antibody will be specific for a cancer cell and may be modified as discussed above. The virus will be a virus that infects cancer cells. The monoclonal antibody and virus may be in dry or liquid form. If the virus and monoclonal antibody are in dry form, the kit may include a solution to solubilize the dried material. The kit may also include transfer factor in liquid or dry form. If the transfer factor is in dry form, the kit will include a solution to solubilize the transfer factor. The kit may also include containers for mixing and preparing the vaccine components. Such kits would include instruction materials for administration of the vaccine. The kit may also include the various needles, tubing, etc., necessary to administer the vaccine.

Treatment Program

The typical treatment program consists of an initial 500 mgm given intravenously in a single bolus followed monthly with 100 mgm infusions for 4 additional months of modified monoclonal antibody, virus or modified viruses. The treatment will generally be followed by the administration of transfer factor either orally or intravenously as discussed above. The transfer factor may be administered before, during or after the administration of monoclonal antibody, virus or modified viruses.

After administration, the patient is monitored clinically with appropriate laboratory tests, CT scans, ultrasound, etc. to ascertain the effectiveness of therapy and to define when therapy is complete and can be discontinued. This procedure could theoretically be applied to the treatment of any cancer for which monoclonal antibodies or infective viruses exist.

The invention will be better understood by way of the following, non-limited examples.

EXAMPLES

Example 1

Patient #1 was diagnosed to have a pancreatic cancer with metastases to the liver showing marked progression of hepatic metastases. The situation was said to be incurable and the treatment goals were palliative.

Computed Tomography (CT) scans of the upper abdomen showed numerous hypodensities scattered throughout all segments of both lobes of the liver of patient #1. All hypodensities measured less than 1 centimeter in diameter. There was a relatively hypodense and amorphous mass with ill-defined margins approximately 2×3×4 centimeters in the areas of the pancreas. The diagnosis at the time was inflammatory or neoplastic disease of the pancreas. The CT focused liver biopsy showed mild hepatic benign inflammatory disease. A repeat CT scan directed biopsy twenty days later showed clear islands of adenocarcinoma in the liver, thus confirming the pancreatic malignancy.

Chemotherapy was begun twenty-six days later and continued weekly for six cycles through one month. After a 14 day break, chemotherapy was given again weekly for 3 weeks. The patient was told that he had, at most, a few months to live, and that the progression of the cancer would continue until death.

The patient was started on a mumps virus vaccine and transfer factor therapy at the end of the 6 cycle chemotherapy period, receiving 1.0 ml of transfer factor (equivalent to $10^8$ lymphocytes) three times a week. Each mumps injection contained a 0.5 ml immunizing dose of live mumps virus vaccine, manufactured by Merck Pharmaceuticals, according to the schedule shown below. (See Table 1—Mumps Vaccine and Transfer Factor Injection Data).

Transfer factor (TF) is obtained from peripheral blood lymphocytes of donors previously sensitized to the aspergillus antigen Asp f1, and from donors who were given immunizing doses of mumps virus vaccine (0.5 ml) two weeks prior to phoresis. The former TF was used with the mab—Asp f1 conjugate therapy. The mumps reactive TF was used in the treatment in which the patient was given mumps virus vaccine before TF.

The lymphocytes are collected by a double leukophoresis at the Stanford Phoresis Center, counted, disrupted by freeze-thaw cycles and dialyzed. The dialysis fluid contains the transfer factor. It is reconstituted to contain the transfer factor obtained from $10^8$ lymphocytes per 1.0 ml of final extract in buffered normal saline. The leukophoresis samples from two donors immunized with mumps vaccine yielded 28 ml and 53 ml of transfer factor, respectively.

The patient began experiencing a reduction in symptoms following the initiation of the injections of the mumps virus and transfer factor materials. A repeat CT scan 14 days after the first injection of mumps virus showed a reduction in the number of low density lesions in the liver. The margins of the pancreatic mass previously reported were more irregular. Several clinicians noted a significant improvement in the patient's clinical state. In addition, the patient's liver function tests results showed a continuous improvement toward normal to a degree not seen with simple chemotherapy treatment. (See Table 2—Liver Function Test Results). At day 23 the liver enzymes increased probably because of the inflammation induced by the killer T-cells. "Alk Phos" is alkaline phosphatase; "GGT" is gamma glutamyl transferase, LDH is lactate dehydrogenase.

A review of the data by the patient's two oncologists and his general internist returned opinions of remarkable improvement, unexpected if it were the result of chemotherapy alone.

TABLE 1

Mumps Vaccine and Transfer Factor Injection Schedule

| Day | Mumps Vaccine | Transfer Factor |
|---|---|---|
| 1 | 0.05 ml + 0.5 ml | |
| 3 | | 1.0 ml |
| 4 | 0.5 ml | 1.0 ml |
| 5 | 0.5 ml | |
| 6 | | 1.0 ml |
| 9 | | 1.0 ml |
| 11 | 0.5 ml | 1.0 ml |
| 12 | 0.5 ml | |
| 13 | | 1.0 ml |
| 16 | | 1.0 ml |
| 18 | 0.5 ml | 1.0 ml |
| 19 | 0.5 ml | |
| 20 | | 1.0 ml |
| 23 | | 1.0 ml |
| 25 | 0.5 ml | 1.0 ml |
| 26 | 0.5 ml | |

TABLE 1-continued

Mumps Vaccine and Transfer Factor Injection Schedule

| Day | Mumps Vaccine | Transfer Factor |
|---|---|---|
| 27 | | 1.0 ml |
| 30 | | 1.0 ml |
| 32 | | 1.0 ml |
| 34 | | 1.0 ml |
| 37 | | 1.0 ml |
| 39 | 0.5 ml | 1.0 ml |
| 40 | 1.0 ml | |
| 41 | | 1.0 ml |

TABLE 2

LIVER FUNCTION TEST RESULTS

| | DAY | | | | | | |
|---|---|---|---|---|---|---|---|
| | 1 | 23 | 41 | 49 | 54 | 75 | 82 | 89 |
| Alk Phos | 74 | 303 | 529 | 411 | 404 | 277 | ND | 206 |
| GGT | 45 | 268 | 530 | 395 | 431 | 378 | ND | 282 |
| SGOT | 45 | 90 | 92 | 85 | 81 | 36 | ND | 34 |
| LDH | ND | 611 | 418 | 363 | 347 | 304 | ND | 217 |
| Bilirubin, Total | 1.2 | 1.7 | 2.8 | 2.2 | 2.2 | 1.6 | ND | 1.3 |
| Amylase | ND | ND | ND | ND | 135 | 97 | 127 | ND |

Example 2

The antigen Asp f1 was conjugated to the monoclonal antibody 17-1A (Panorex) from the National Cancer Institute. Panorex was chosen because it was commercially available and had monoclonal antibody activity against the pancreas. Once the Panorex and Asp f1 were combined, skin tests were performed on patient #1 with Panorex alone, Panorex plus Asp f1 and with Asp f1 alone. The patient showed a negative response to the monoclonal antibody, a strongly positive response to pure Asp f1 and an equally strong response to the Asp f1 conjugated monoclonal antibody at 48 and 72 hours.

The Asp f1 conjugate was administered to the patient following the standard protocol for the procedure for administration of the monoclonal antibody Herceptin available from Genentech. The procedure is as follows:

Dosage and Administration

The recommended initial loading dose is 4 mg/kg Asp f1 conjugate administered as a 90-minute infusion. The recommended weekly maintenance dose is 2 mg/kg Asp f1 conjugate and can be administered as a 30-minute infusion if the initial loading dose is well tolerated. The Asp f1 conjugate may be administered in an outpatient setting.

Preparation for Administration

Appropriate aseptic technique is utilized. Each vial of Asp f1 conjugate is reconstituted with 20 mL of BWFI, (Bacteriostatic Water for Injection), USP, 1.1% benzyl alcohol preserved to yield a multi-dose solution containing 21 mg/mL Asp f1 conjugate. If the patient has known hypersensitivity to benzyl alcohol, the Asp f1 conjugate must be reconstituted with sterile water for Injection. The amount (mg) of Asp f1 needed, based on a loading dose of 4 mg Asp f1/kg body weight or a maintenance dose of 2 mg Asp f1 conjugate/kg body weight is determined. Next, the volume of 21 mg/mL Asp f1 solution is calculated, withdraw from the vial and added to an infusion bag containing 250 mL of 0.9% sodium chloride, USP. Dextrose (5%). The bag is then gently inverted to mix the solution.

Administration

Treatment is administered in an outpatient setting by administration of a 4 mg/kg Asp-f1 conjugate by loading dose by intravenous (IV) infusion over 90 minutes. Transfer factor was administered as described in Example 1. Patient #1 was observed for fever and chills and some chills were noted.

Results

After administration of Asp f1 conjugate, the patient continued living. He exhibited improved overall symptoms although he had been told that he had, at most, a few months to live.

During the immunotherapy treatment program, the patient was also simultaneously treated by an oncologist. During the patient's treatment with Asp f1 conjugate, the oncologist administered chemotherapy in the amount of 5 flurouracil (FU.) This treatment is very toxic to lymphocytes. After the treatment, the patient went into rapid decline (presumably as a result of the killing off of the patient's lymphocytes by the administration of the 5FU) and died 2 weeks later. Thus, the administration of the compositions of this invention should be carefully monitored when used in combination with traditional chemotherapy.

I claim:

1. A composition comprising a monoclonal antibody directed to a cancer cell and transfer factor wherein the monoclanal antibody is conjugated to a fungal antigen or mumps virus.

2. The composition according to claim 1 wherein the cancer cell is selected from the group consisting of lung cancer cell, pancreas cancer cell, liver cancer cell, cervical cancer cell, kidney cancer cell, brain cancer cell, breast cancer cell, and spleen cancer cell.

3. The composition according to claim 2 wherein the cancer call is a pancreas cancer cell.

4. The composition according to claim 1 wherein the fungal antigen is asp f1.

5. The composition according to clam 1 wherein the monoclonal antibody is selected from the group consisting of 17-1A, CC49, EGFr surface factor, anti MC-10 antigen, anti-HER2, anti-CD20, NR-LU-10 and MDX-H210.

6. A kit comprising a monoclonal antibody directed to a cancer cell and a transfer factor wherein the monoclonal antibody is conjugated to a fungal antigen or mumps virus.

7. The kit according to claim 6 wherein the fungal antigen is asp f1.

8. The composition of claim 1, wherein the fungal antigen is an aspergillus antigen.

9. The kit of claim 6, wherein the fungal antigen is an aspergillus antigen.

* * * * *